US008699138B2

(12) United States Patent
Cogger et al.

(10) Patent No.: US 8,699,138 B2
(45) Date of Patent: Apr. 15, 2014

(54) MULTI-WAVELENGTH MULTI-LAMP RADIATION SOURCES AND SYSTEMS AND APPARATUSES INCORPORATING SAME

(75) Inventors: Jeffrey Cogger, Vergennes, VT (US); James Hermanowski, Waterbury, VT (US); Joel Melnick, Waltham, VT (US)

(73) Assignee: Nathaniel Group, Inc., Vergennes, VT (US)

( * ) Notice: Subject to any disclaimer, the term of this patent is extended or adjusted under 35 U.S.C. 154(b) by 46 days.

(21) Appl. No.: 13/486,082

(22) Filed: Jun. 1, 2012

(65) Prior Publication Data

US 2012/0307512 A1  Dec. 6, 2012

Related U.S. Application Data

(60) Provisional application No. 61/491,986, filed on Jun. 1, 2011.

(51) Int. Cl.
*G02B 27/10* (2006.01)
*G02B 26/08* (2006.01)
*G02B 26/00* (2006.01)

(52) U.S. Cl.
USPC ............................ 359/618; 359/298; 359/290

(58) Field of Classification Search
USPC ................... 359/811–830, 290–298, 611–630
See application file for complete search history.

(56) References Cited

U.S. PATENT DOCUMENTS

| 4,418,689 | A | 12/1983 | Kanazawa |
| 7,330,314 | B1 | 2/2008 | Cobb |
| 7,969,644 | B2 * | 6/2011 | Tilleman et al. ............... 359/298 |
| 8,102,580 | B2 * | 1/2012 | Duncan ....................... 359/196.1 |
| 8,129,670 | B2 * | 3/2012 | Laycock et al. ........... 250/208.1 |
| 2005/0047172 | A1 | 3/2005 | Sander |
| 2010/0228089 | A1 | 9/2010 | Hoffman et al. |

OTHER PUBLICATIONS

International Search Report and Written Opinion dated Jan. 3, 2013, issued in connection with related PCT/US2012/040411 filed Jun. 1, 2012.

\* cited by examiner

*Primary Examiner* — Mohammed Hasan
(74) *Attorney, Agent, or Firm* — Downs Rachlin Martin PLLC

(57) ABSTRACT

Systems for providing high-intensity and high-quality illumination and other electromagnetic radiation (EMR) to target regions. The systems each include multiple EMR sources and a radiation combiner for combining the output radiation of the multiple sources. In some examples, the EMR sources are visible light sources, such as light-emitting diodes and laser diodes. In some of those examples, the light sources are of differing colors that are combined to form output illumination having user-selected qualities, such as color and intensity. The output of the radiation combiner can be directed into an optical fiber or bundle of optical fibers for remote delivery of the output to a target, such as in endoscopy and remote-illumination microscopy. Systems disclosed can also include additional EMR beams, such as visible light beams used for pointing/targeting and non-visible beams used, for example, for heating and fluoroscopic excitation of dyes/stains, among other things.

13 Claims, 6 Drawing Sheets

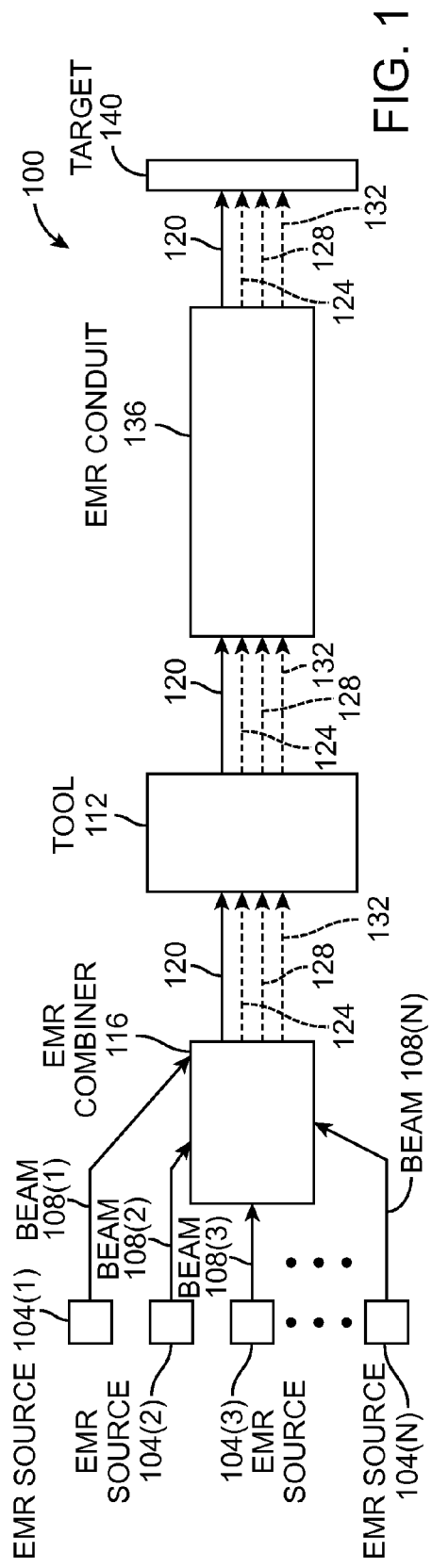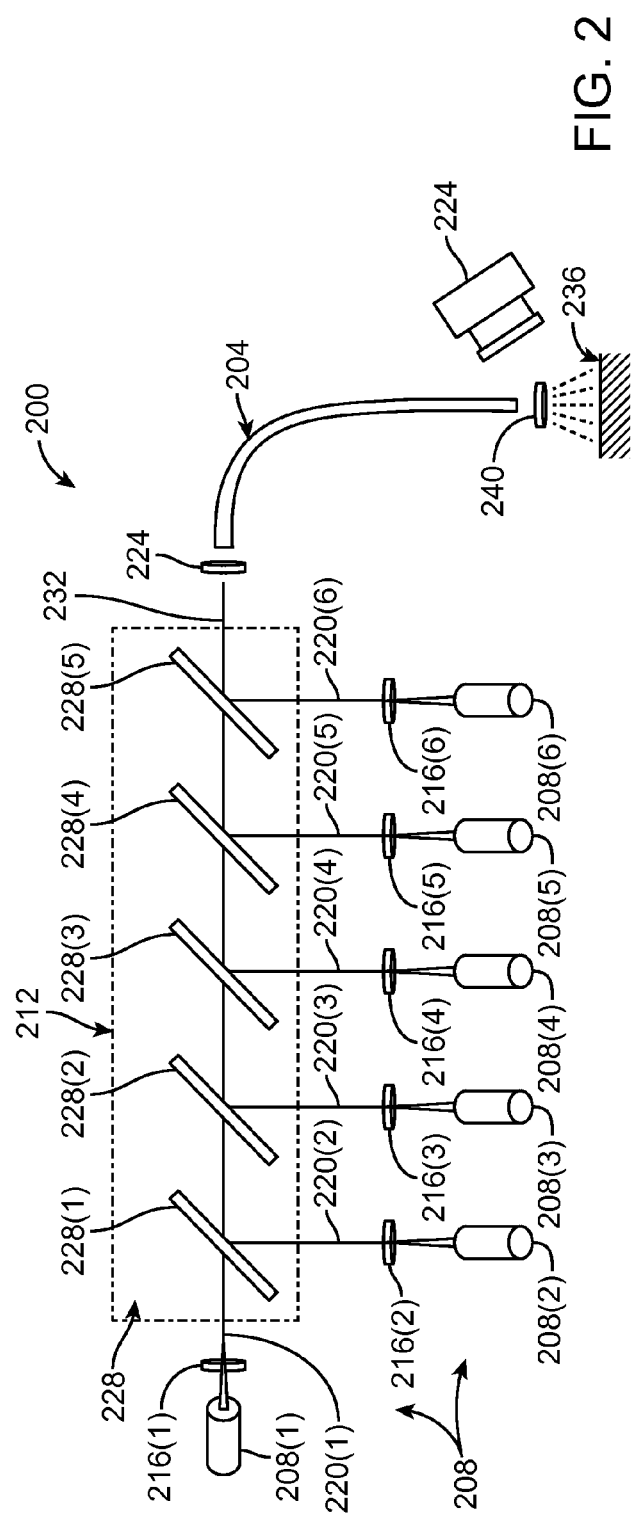

MULTI-WAVELENGTH MULTI-LAMP RADIATION SOURCES AND SYSTEMS AND APPARATUSES INCORPORATING SAME

RELATED APPLICATION DATA

This application claims the benefit of priority of U.S. Provisional Patent Application Ser. No. 61/491,986, filed on Jun. 1, 2011, and titled "Multi-Wavelength Multi-Lamp Source And Means For Speckle Reduction In Optical Illumination," which is incorporated by reference herein in its entirety.

FIELD OF THE INVENTION

The present invention generally relates to the field of illumination. In particular, the present invention is directed to multi-wavelength multi-lamp radiation sources and systems and apparatuses incorporating same.

BACKGROUND

High intensity and high quality illumination of small regions is desirable in a number of fields, such as endoscopy and microscopy. However, many challenges exist in developing illumination systems capable of providing the desired illumination in not only a cost-effective manner, but also in a way that the systems are compact and the illumination is safe for the eyes of the viewer and the target, such as living tissue, being illuminated.

SUMMARY OF THE DISCLOSURE

In one implementation, the present disclosure is directed to an apparatus for providing input light to a tool that uses the input light to illuminate a target region. The apparatus includes a coherent light source designed and configured to provide coherent light; an incoherent light source designed and configured to provide incoherent light; an electromagnetic-radiation (EMR)-combiner designed and configured to combine the coherent light and the incoherent light with one another into a combined beam; and a first focusing optic designed and configured to focus the combined beam so as to provide the input light to the tool.

In another implementation, the present disclosure is directed to a system including a tool designed and configured to illuminate an illumination region using input light, the tool including an input for receiving the input light; an illumination-light source designed and configured to provide the input light to the tool, the illumination-light source comprising: a plurality of light sources designed and configured for providing a plurality of light beams of differing wavelengths; an electromagnetic-radiation (EMR)-combiner designed and configured to combine the plurality of light beams with one another into a combined beam; and a first focusing optic designed and configured to focus the combined beam so as to provide the input light to the tool.

In still another implementation, the present disclosure is directed to a system for applying focused electromagnetic radiation (EMR) to a target so as to perform work on the target. The system includes an illuminating-light source designed and configured to provide illuminating light; a work-EMR source designed and configured to provide a work-EMR beam; a pointing-light source designed and configured to provide a pointing-light beam; a tool that comprises: a first EMR input; a second EMR input; a work end that includes: a negative lens designed and configured for diverging the illuminating light so as to illuminate the target; and a positive lens designed and configured for focusing the work-EMR beam and the pointer-light beam so that the pointing-light beam indicates the location of the work-EMR beam; a first EMR conduit extending between the first EMR input and the negative lens; and a second EMR conduit extending between the second EMR input and the positive lens; and an EMR-guide designed and configured to: guide the illuminating light to the first EMR input; and combine the work-EMR beam and the pointing-light beam with one another and guide the work-EMR beam and the pointing-light beam to the second EMR input.

In yet another implementation, the present disclosure is directed to a system including a first optical tool; a plurality of light sources designed and configured for providing a plurality of light beams of differing wavelengths; an electromagnetic-radiation (EMR)-combiner designed and configured to combine the plurality of light beams with one another into a combined beam and to output at least one output beam; and at least one focusing optic designed and configured to focus the at least one output beam so as to provide the input light to the first optical tool.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 1 is a high-level schematic diagram of an electromagnetic-radiation (EMR) generation and delivery system that includes multiple EMR sources, an EMR combiner, and at least one tool that utilizes the EMR from the EMR sources;

FIG. 2 is a diagram of a first exemplary system based on the system of FIG. 1, in which the EMR combiner comprises a plurality of partial mirrors in series with one another and in which the tool is a fiberscope;

DETAILED DESCRIPTION

Figure 3:
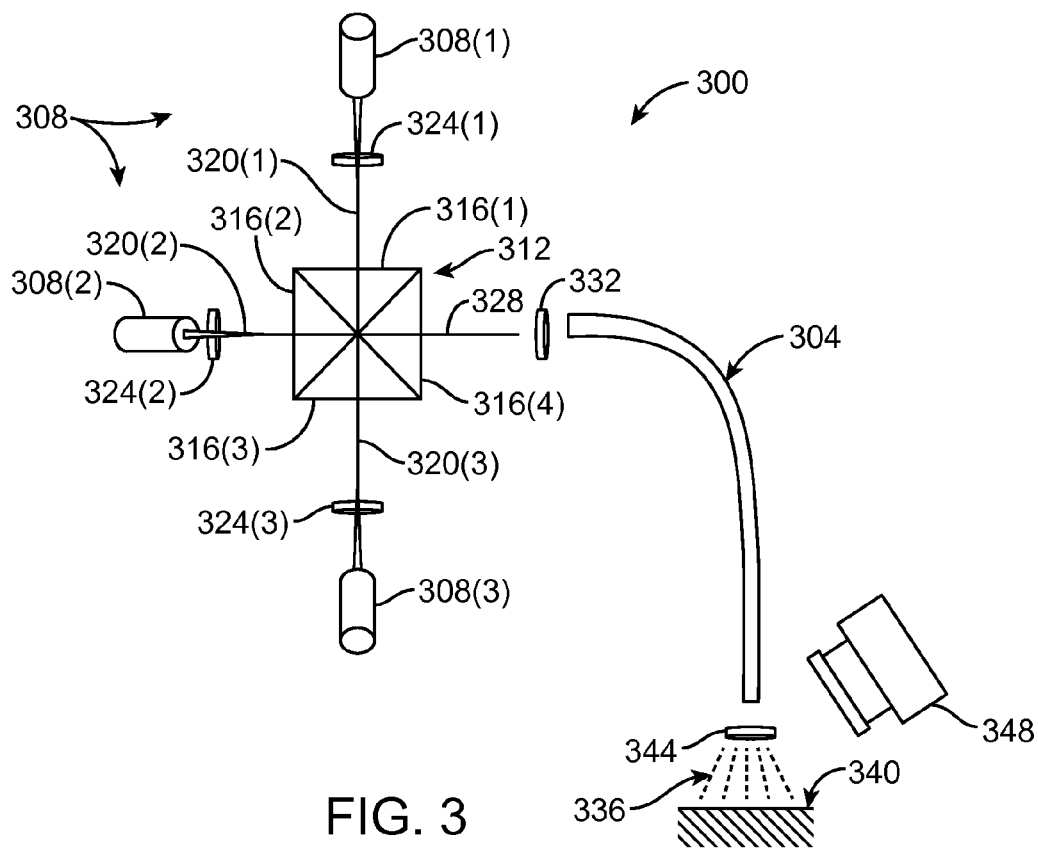
FIG. 3 is a diagram of a second exemplary system based on the system of FIG. 1, in which the EMR combiner comprises a plurality of specially coated prisms and in which the tool is a fiberscope.

Referring now to the drawings, FIG. 1 illustrates an exemplary electromagnetic-radiation (EMR) generation and delivery system 100 that incorporates features and aspects of the present invention. As will be described below in conjunction with a number of specific exemplary embodiments, benefits of system 100 include, but are not necessarily limited to, the ability to provide illumination (optical, ultraviolet, infrared, etc.) that is high-intensity, adjustable in intensity, high-quality, speckle-free, color-tunable, and/or color-accurate; to provide such illumination via a compact system; to provide such illumination in conjunction with pointer/targeting beams, heating beams, and/or laser ablation beams; and to provide such EMR via optical fibers/fiber bundles that can be relatively small so as to have minimal impact on the environment(s) in which the optical fibers/fiber bundles are intended to operate. These and other benefits of a system made in accordance with the present invention, such as system 100 of FIG. 1, will become readily apparent after reading this entire disclosure.

System 100 includes multiple EMR sources, here EMR sources 104(1) to 104(N) that provide corresponding respective EMR beams 108(1) to 108(N), and one or more tools 112 (a single tool is shown for convenience) that utilize the EMR beams in any of a variety of combinations. As illustrated below by a number of detailed examples, the types of EMR sources 104(1) to 104(N) and corresponding types of EMR beams 108(1) to 108(N) will vary depending on the type(s) of tool(s) 112 and the application at hand. Examples of tools that each of tools 112 can be, include, but are not limited to, fiberscopes (e.g., endoscopes), microscope illumination source, spot heating devices, laser-ablation devices, combinations thereof, and other types of devices requiring EMR of a certain quality(ies) and/or character(s).

System 100 also includes an EMR combiner 116 that combines some or all EMR beams 108(1) to 108(N) of the various EMR sources 104(1) to 104(N) into one or more combined beams 120 that are then provided to the corresponding respective tools 112. As seen from the several detailed examples below, EMR combiner 116 can take any of a variety of forms, with several being illustrated in FIGS. 2-8. Depending on the configuration of the system at issue and the application at hand, non-illumination EMR beams that may also be generated by system 100, such as a pointer/targeting beam 124, heating beam 128, a laser-ablation beam 132, etc., may not necessarily be combined into combined beam 120, but rather may be physically separate from the combined beam, as shown in FIG. 1 for convenience.

In the example shown in FIG. 1, an EMR conduit 136 is provided to conduct each of beams 120, 124, 128, and 132, as they may or may not be present in any given system, to a desired location, for example, a point proximate a target 140 desired to be irradiated with the beam(s). In some embodiments, conduit 136 is part of tool 112, and in others it is not. As eluded to above, optical conduit 136 can be, for example, a single optic fiber, bundle of optic fibers, or other EMR conducting element(s) largely conductive at the one or more wavelengths at issue. As mentioned above, if EMR conductor 136 includes multiple conducting elements, in some cases one or more of beams 120, 124, 128, and 132 may be carried by one (or one set) of such conducting elements and one or more others of the beams may be carried by another (or another set) of such conducting elements. Those skilled in the art will readily appreciate the variety of ways that EMR conduit can be configured.

Depending on the application of system 100, target 140 can be any of a variety of things. It is noted that the term "target" is intended very generally to mean anything that the user(s) (not shown) of system 100 intends to be irradiated with the one or more beams 120, 124, 128, and 132 as they may be present in any particular system. Examples of target 140 include, but by no means are limited to, living tissue/cells, a cancer mass/cells, dead tissue, a microscope specimen, and a workpiece or other object, among many others.

With some of the broad aspects and features having been introduced, attention is now directed to FIG. 2, which illustrates a first exemplary system 200 that is based on system 100 of FIG. 1. As seen in FIG. 2, system 200 includes a fiberscope 204 (e.g., an endoscope), a plurality of light sources 208, here light sources 208(1) to 208(6), and an EMR combiner 212. In one example, at least one of light sources 208 is a source of coherent white light, such as a white light-emitting diode (LED), deuterium lamp, or a xenon arc source, among others. Other ones of light sources 208 can each be an individual laser (or group of lasers) of a specific wavelength, with differing ones of these other light sources emitting light at differing wavelengths. In some applications, such as endoscopy for example, coherent white light is desired for its color temperature and lack of speckle, while the combined laser beams add brightness. In this example, an input focusing optic 216(1) to 216(6), such as a single lens or multiple lenses in one or more groupings, is provided for each light source 208(1) to 208(6) to focus the output of that light source into a focused beam 220(1) to 220(6) that is directed into EMR combiner 212, which in this example is a light combiner since all of the EMR beams at issue are light beams. As those skilled in the art will readily appreciate, each input focusing optic 216(1) to 216(6) can be integrated with the corresponding light source 208(1) to 208(6) or it can be separate from it.

In this example, EMR combiner 212 includes an output focusing optic 224 and a plurality of specially coated mirrors 228, here, five mirrors 228(1) to 228(5), that direct focused beams 220(2) to 220(6) to the output focusing optic and allow focused beam 220(1) and corresponding one(s) of any upstream focused beams 220(2) to 220(6) to pass therethrough. It is noted that mirrors 228 and focused beams 220 (1) to 220(6) in this example are arranged and oriented so that the focused beams are coincident with one another and the mirrors are oriented at 45° relative to the beams. Those skilled in the art will readily understand how to select and arrange mirrors 228 to accommodate other arrangements and orientations of focused beams 220(1) to 220(6). Output focusing optic 224 directs a combined beam 232, which is the combination of focused beams 220(1) to 220(6), to fiberscope 204, which includes one or more optical fibers. Like input focusing optics 216(1) to 216(6), output focusing optic 224 may include one or more lenses organized into one or more optical groupings. Fiberscope 204 conducts combined beam 232 to a working end 204 of the fiberscope, where the combined beam is then directed to an illuminated object (target) 236, here using an illuminating optic 240. As those skilled in the art will readily appreciate, illuminating optic 240 may include one or more lenses grouped into one or more optical groupings and desired/needed to achieve a desired result. System 200 further includes an imaging device 244 to capture one or more images and/or video of illuminated object 236. Imaging device 244 can be any suitable imaging device, such as an image sensor, a camera, a fiber optic/optic bundle routed to an analytic device, monitor, image sensor, etc., and a microscope, among other things, and any suitable combination thereof. Details of such devices need not be provided herein, as they are well-known in the art.

FIG. 3 illustrates a second exemplary system 300 that is based on system 100 of FIG. 1. System 300 of FIG. 3 is similar to system 200 of FIG. 2 in that it has a fiberscope 304, a plurality of light sources 308, and an EMR combiner 312. However, in system 300 of FIG. 3, there are three light sources 308(1) to 308(3), instead of the six in system 200 of FIG. 2, and EMR combiner 312 comprises specially coated prisms 316(1) to 316(4) instead of mirrors, as in system 200. In this example, each light source 308(1) to 308(3) is a laser, whose corresponding output beam 320(1) to 320(3) is directed into EMR combiner 312 as shown using a suitable focusing optic 324(1) to 324(3).

In this example, EMR combiner 312 has prisms 316(1) to 316(4) arranged in the form of an "X," allowing three different light beams 320(1) to 320(3) to be combined. The output 328 of EMR combiner 312 is focused using a focusing optic 332 onto fiberscope 304, which may comprise an optical fiber or fiber bundle. The radiation output 336 from fiberscope 304 is then focused on an illuminated object 340 using another focusing optic 344. As with the various focusing optics illustrated in FIG. 2, each focusing optic 324(1) to 324(3) can include one or more lenses organized into one or more groupings, as known in the art. System 300 further includes an imaging device 348 to capture one or more images and/or video of illuminated object 340. Imaging device 348 can be any suitable imaging device, such as, an image sensor, a camera, a fiber optic/optic bundle routed to an analytic device, monitor, image sensor, etc., and a microscope, among other things, and any suitable combination thereof. Again, details of such devices need not be provided herein, as they are well-known in the art.

Figure 4:
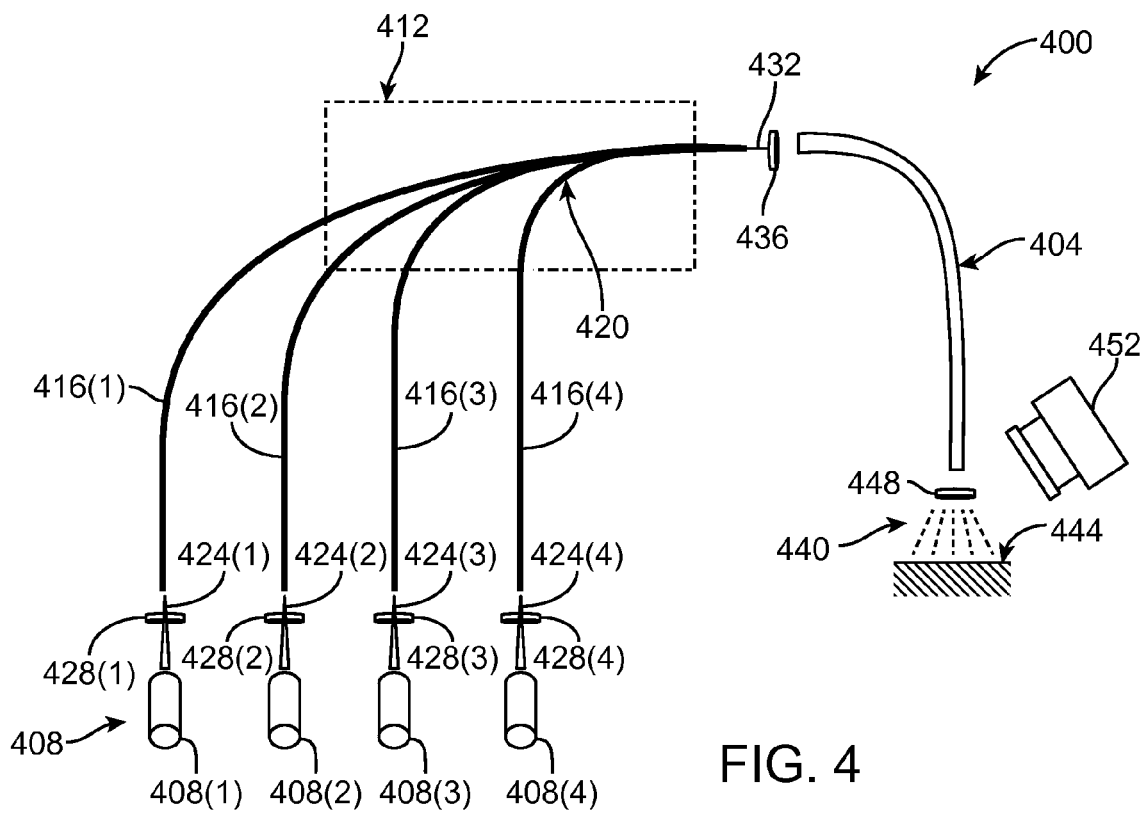
FIG. 4 is a diagram of a third exemplary system based on the system of FIG. 1, in which the EMR combiner comprises an optical junction of conducting fibers and in which the tool is a fiberscope.

FIG. 4 illustrates a third exemplary system 400 that is based on system 100 of FIG. 1. System 400 of FIG. 4, like systems 200 and 300 of FIGS. 2 and 3, respectively, includes a fiberscope 404, a plurality of light sources 408, and an EMR combiner 412. Primary differences, though, are that system 400 has four light sources 408(1) to 408(4), and EMR combiner 412 comprises four optic fibers 416(1) to 416(4) that come together at an optical junction 420. Optical junction 420 combines the beams 424(1) to 424(4) from light sources 408(1) to 408(4) into a combined beam 420 that is output to fiberscope 404. In this example, each light source 408(1) to 408(4) is a laser, whose corresponding output beam 424(1) to 424(4) is directed into a respective one of optic fibers 416(1) to 416(4) of EMR combiner 412 as shown using a suitable focusing optic 428(1) to 428(4).

The output 432 of EMR combiner 412 is focused using a focusing optic 436 onto fiberscope 404, which may comprise an optical fiber or fiber bundle. The radiation output 440 from fiberscope 408 is then focused on an illuminated object 444 using another focusing optic 448. As with the various focusing optics illustrated in FIGS. 2 and 3, each focusing optic 424(1) to 424(4) can include one or more lenses organized into one or more groupings, as known in the art. System 400 further includes an imaging device 452 to capture one or more images and/or video of illuminated object 440. Imaging device 452 can be any suitable imaging device, such as, an image sensor, a camera, a fiber optic/optic bundle routed to an analytic device, monitor, image sensor, etc., and a microscope, among other things, and any suitable combination thereof. Again, details of such devices need not be provided herein, as they are well-known in the art. It is noted that an optical-junction type EMR combiner can also be formed in manners other than the manner shown, for example, by using a planar structure, whereby the junction of the individual radiation transporting media is formed on a flat surface with a means of coupling radiation to it, for example by fiber optic connectors.

Figure 5:
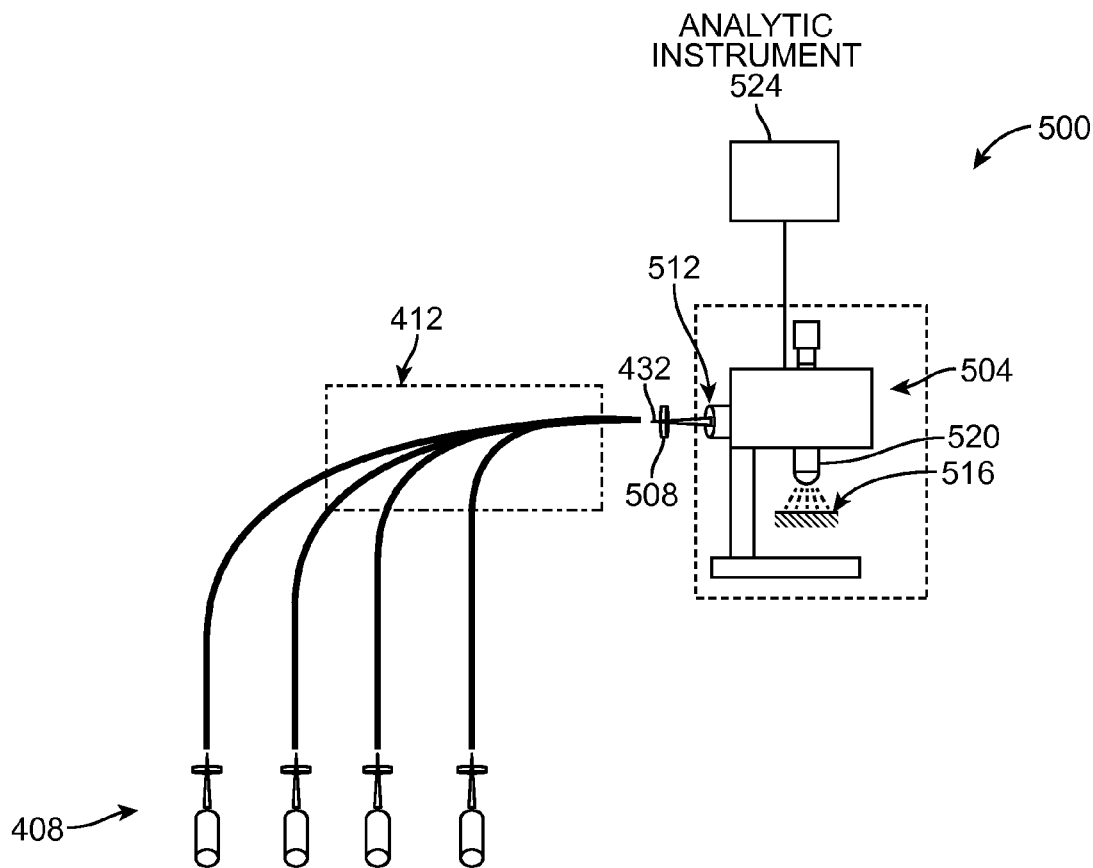
FIG. 5 is a diagram of a fourth exemplary system based on the system of FIG. 1, in which the EMR combiner comprises an optical junction of conducting fibers and in which the tool is a microscope.

FIG. 5 illustrates a fourth exemplary system 500 that utilizes EMR combiner 412 and light sources 408 of FIG. 4, but has in place of fiberscope 404 of FIG. 4 a microscope 504. The output of EMR combiner 412 of FIG. 5, i.e., combined beam 420, is focused using a suitable focusing optic 508 onto an illumination aperture 512 of microscope 504. The radiation of the now-focused combined beam 420 is then directed inside microscope 504 to illuminate an object 516 being magnified by the microscope. An image (not shown) of illuminated object 516 can then be captured using an objective lens 520 of microscope 504 and directed to a suitable imaging device, image-capturing device, and/or and analytical instrument 524 for viewing, image-acquisition, and/or analysis. In some embodiments, each light source 408 may consist of an individual laser of a specific wavelength or of multiple lasers in parallel. Those skilled in the art will readily appreciate that EMR combiner 412 is depicted merely as an example and that any EMR combiner can be used, such as, for example, any one of EMR combiners 212, 312, 604, 704, and 804 of FIGS. 2, 3, 6, 7 and 8, may be used.

Figure 6:
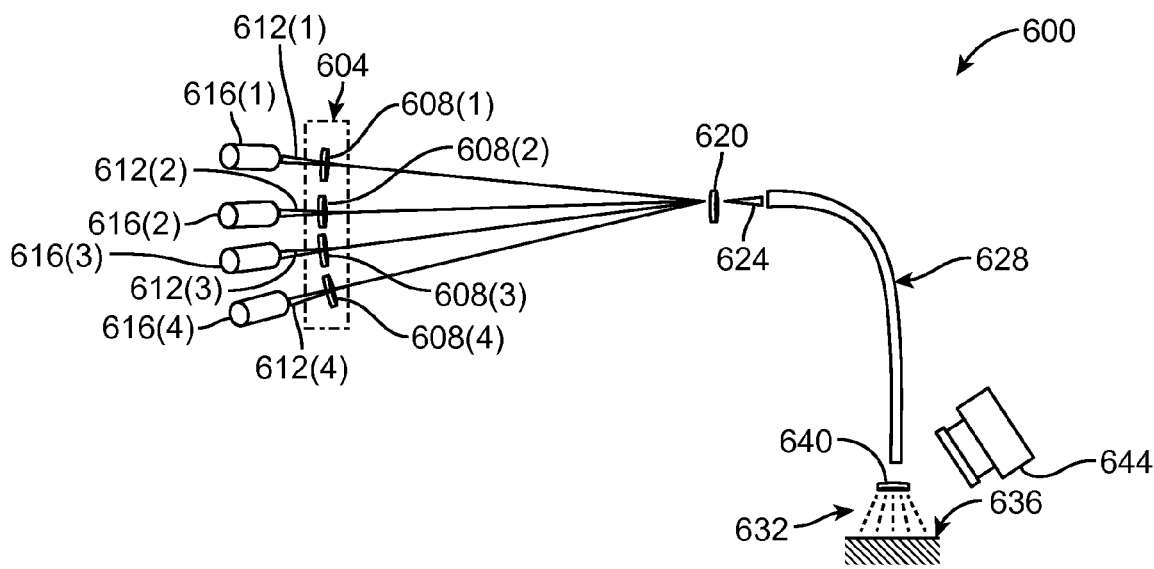
FIG. 6 is a diagram of a fifth exemplary system based on the system of FIG. 1, in which the EMR combiner comprises a plurality of focusing/directing optics and in which the tool is a fiberscope.

FIG. 6 shows a fifth exemplary system 600 that illustrates a further variation of EMR combiner 116 illustrated generically in FIG. 1. As seen in FIG. 6, system 600 includes an EMR combiner 604 comprising a plurality of focusing/directing optics, here optics 608(1) to 608(4), for focusing and directing the output beams, here output beams 612(1) to 612(4), of a plurality of light sources, here light sources 616(1) to 616(4), only a focusing optic 620 that, in turn, focuses the combinations of the individual focused and directed output beams onto an optical mixing rod 624. Optical mixing rod 624 is oriented toward the face of a light transmitting medium, which is shown as an optical fiber endoscope 628. The radiation 632 output from endoscope 628 is focused on an object 636 using a suitable focusing optic 640, which can be the same as any of the similarly situated focusing optics noted above. An image (not shown) of the now illuminated object 636 is then captured using an imaging device 644 to capture one or more images and/or video of illuminated object 636. Imaging device 644 can be any suitable imaging device, such as, an image sensor, a camera, a fiber optic/optic bundle routed to an analytic device, monitor, image sensor, etc., and a microscope, among other things, and any suitable combination thereof. Details of such devices need not be provided herein, as they are well-known in the art. Each light source 616(1) to 616(4) may consist of an individual laser of a specific wavelength or of multiple lasers in parallel.

Figure 7:
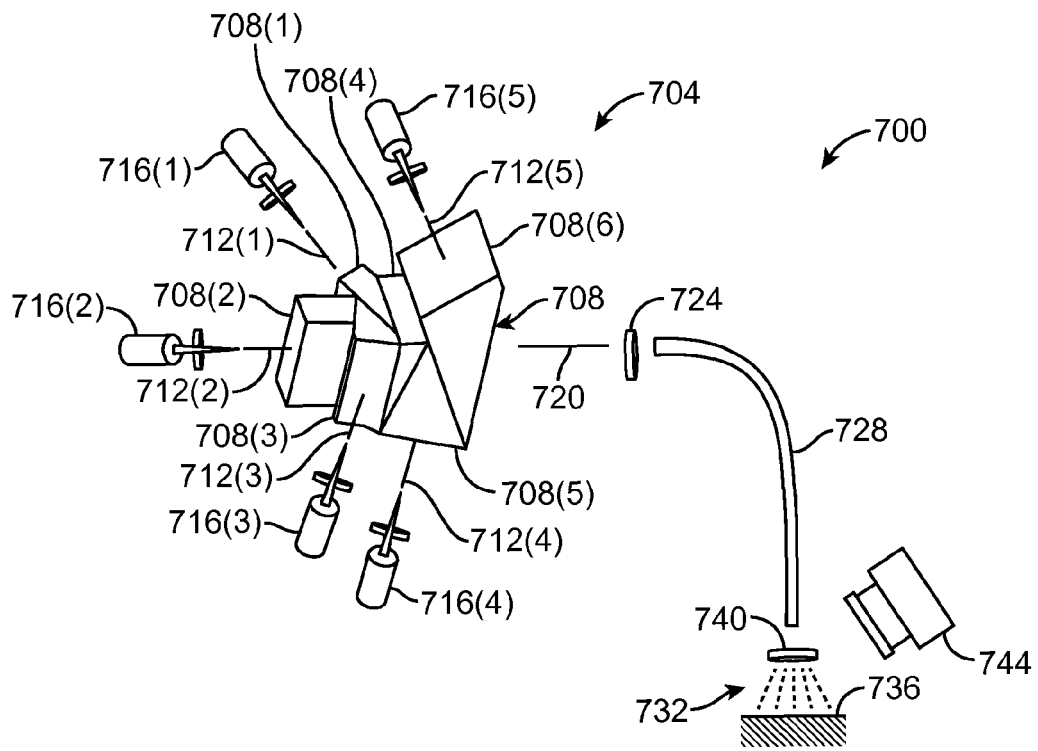
FIG. 7 is a diagram of a sixth exemplary system based on the system of FIG. 1, in which the EMR combiner comprises a compound prism and in which the tool is a fiberscope.

FIG. 7 illustrates a sixth exemplary system 700 having another type of EMR combiner 704 than systems 200, 300, 400, 500, and 600 of FIGS. 2 through 6, respectively. In system 700, EMR combiner 704 comprises a compound prism 708 that in this example is composed of six individual prisms 708(1) to 708(6) that are designed and configured to receive five beams 712(1) to 712(5) from five differing light sources 716(1) to 716(5) and five differing directions and combine them into a combined output beam 720. In this example, light sources 716(1) to 716(5) are high-intensity light sources, three of which (light sources 716(1) to 716(3) are red, green, and blue solid state lasers each comprising 20 individual laser generators per beam 712(1), 712(2), 712(3). Red, green, and blue beams 712(1), 712(2), and 712(3) mix to form white light that system 700 uses for general illumination purposes. Light source 716(4) comprises a white LED that EMR combiner 704 mixes with the laser light from light sources 716(1) to 716(3) to reduce the effect of speckle from those laser light sources by filling in the dark spots caused by interference of the coherence of laser beams 712(1) to 712(3). Light source 716(5) comprises a deuterium lamp, which in this example provides ultraviolet radiation used as both an ultraviolet radiation reference due to its stability and an excitation source for fluorescence imaging.

Each of the smaller prisms 708(1) to 708(4) consists of shaped glass with antireflective coatings and band pass filters to allow the appropriate color(s) to pass while blocking other colors. In one implementation, prisms 708(1) to 708(6) were manufactured by Optec s.p.a., Milan, Italy. In this example, combined output beam 720 is directed to a focusing optic 724, which directs the beam into a light transmitting medium, which is shown as being an optical fiber endoscope 728. The radiation output 732 from endoscope 728 is then directed onto an object 736 using a suitable optic 740, such as a single lens or multi-lens arrangement. An image (not shown) of the now illuminated object 736 is then captured using an imaging device 744 to capture one or more images and/or video of illuminated object 736. Imaging device 744 can be any suitable imaging device, such as, an image sensor, a camera, a fiber optic/optic bundle routed to an analytic device, monitor, image sensor, etc., and a microscope, among other things, and any suitable combination thereof. Details of such devices need not be provided herein, as they are well-known in the art.

Figure 8:
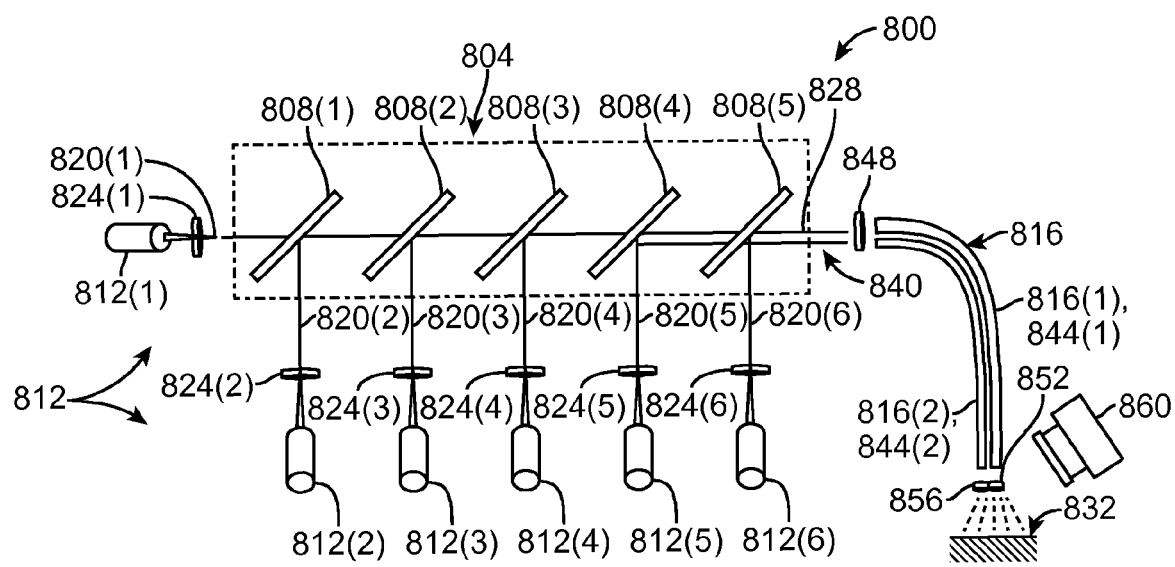
FIG. 8 is a diagram of a seventh exemplary system that is similar to the first exemplary system of FIG. 2 but further includes a laser-targeted infrared heating feature.

FIG. 8 illustrates a seventh exemplary system 800 that utilizes an EMR combiner 804 that has the same basic configuration as EMR combiner 212 of system 200 of FIG. 2. Referring to FIG. 8, EMR combiner 804 includes a plurality of specially coated mirrors 808(1) to 808(5) arranged to reflect and transmit radiation from a plurality of electromagnetic radiation sources 812, here, sources 812(1) to 812(6), in accordance with principles well known to those skilled in the art. System 800 also includes a fiberscope 816 (e.g., an endoscope). In this example, radiation sources 812(1) to 812(3) are high-brightness lamps comprising solid state lasers that provide red, green, and blue output light beams 820(1) to 820(3), respectively. In the embodiment shown, output light beams 820(1) to 820(3) are directed toward EMR combiner 804 using suitable corresponding optics 824(1) to 824(3), which may be focusing optics. EMR combiner 804 combines red, green, and blue laser beams 820(1) to 820(3) to form white light for general illumination.

Radiation source 812(4) comprises an invisible ultraviolet radiation source that provides an ultraviolet beam 820(4) to a corresponding optic 824(4) that directs to EMR combiner 804, which mixes beam 820(4) with red, green, and blue laser beams 820(1) to 820(3) from radiation sources 812(1) to 812(3) to form a general-illumination beam 828. Ultraviolet beam 820(4) is provided in this embodiment as an excitation source for fluorescent examination of an object, here object 832. Due to the presence of the white light and the ultraviolet radiation, general-illumination beam 828 provides visible illumination and ultraviolet excitation.

In this example, radiation source 812(5) is a second green laser source that provides a green laser beam 820(5) that system 800 uses as a pointer beam 836 that provides a spot (not shown) of illumination on object 832. As those skilled in the art will readily appreciate, a user can use this pointer/targeting spot for any one or more of a variety of purposes, including a visual reference to determine whether or not fiberscope 816 is pointing at the correct location on object 832, a guide for determining whether other radiation (see below) is impinging upon the object, etc. Second green laser beam 820(5) is directed into EMR combiner 804 via a suitable optic 824(5) in a manner that second green laser beam 820(5) remains distinct from general-illumination beam 828 formed by the combination of radiation beams 820(1) to 820(4).

System 800 of this example also includes a sixth radiation source, in this case an infrared laser 812(6) that provides an invisible infrared beam 820(6) that allows a user to apply heat to object. Infrared beam 820(6) is directed into EMR combiner 804 via a suitable optic 824(6) in a manner that infrared beam 820(6) remains distinct from general-illumination beam 828 formed by the combination of radiation beams 820(1) to 820(4). As will be understood from the following description, the particular configuration of system 800 provides for focused spot heating of object. However, in alternative embodiments, system 800 can be configured to apply heat from infrared beam is a less-focused, i.e., more spread-out, manner, as desired.

In this example, fiberscope 816 includes two radiation paths 816(1) and 816(2), the first (i.e., path 816(1)) for conducting general-illumination beam 828 from the output 840 of EMR combiner 804 to object 832 and the second (i.e., path 816(2)) for conducting green pointer beam 820(5) and infrared beam 820(6) from the output of the EMR combiner to the object. In the embodiment shown, paths 816(1) and 816(2) are provided by separate corresponding respective radiation-conducting fibers or fiber bundles 844(1) and 844(2). In one instantiation, fiber/fiber bundle 844(1) is constructed in a manner known in the art so as to reduce coherence of general-illumination beam 828, and fiber/fiber bundle 844(2) is constructed in a manner known in the art so as to maintain the coherence of green pointer beam 820(5) and infrared heating beam 820(6). It is noted that in other embodiments, paths 816(1) and 816(2) might be located together in a single conductor/bundle and in yet other embodiments green pointer and infrared heating beams 820(5) and 820(6) can be conducted along paths separate from one another. Those skilled in the art will also readily appreciate that while pointer beam 820(5) is green in this example, other color(s) can be used. Similarly, infrared heating beam 820(6) can be replaced and/or supplemented with one or more other types of radiation beams according to the application of the system. Moreover, depending on the nature and purpose of the beam(s) that replace(s) infrared heating beam 820(6) when such replacement is made, a corresponding pointer need not be used, for example, when one or more of the replacement beams is/are in the visible-light regime and/or causes visible light emission from object 832.

General-illumination beam 828 and green pointer and infrared heating beams 820(5) and 820(6) can be directed into fiberscope 816 using one or more suitable optics, here optic 848. Similarly, beams 828, 820(5), and 820(6) can be directed toward object 832 using any suitable optic, here optic 852 for general-illumination beam 828 and optic 856 for green pointing and infrared beams 820(5) and 820(6). In this example, optic 852 is a dispersing optic that spreads general-illumination beam 828 out for broad-area illumination. Optic 856, on the other hand, is a converging optic that focuses green pointing and infrared beams 820(5) and 820(6) into concentrated spots.

System 800 further includes an imaging device 860 to capture one or more images and/or video of illuminated object 832. Imaging device 860 can be any suitable imaging device, such as, an image sensor, a camera, a fiber optic/optic bundle routed to an analytic device, monitor, image sensor, etc., and a microscope, among other things, and any suitable combination thereof. Details of such devices need not be provided herein, as they are well-known in the art.

Figure 9:
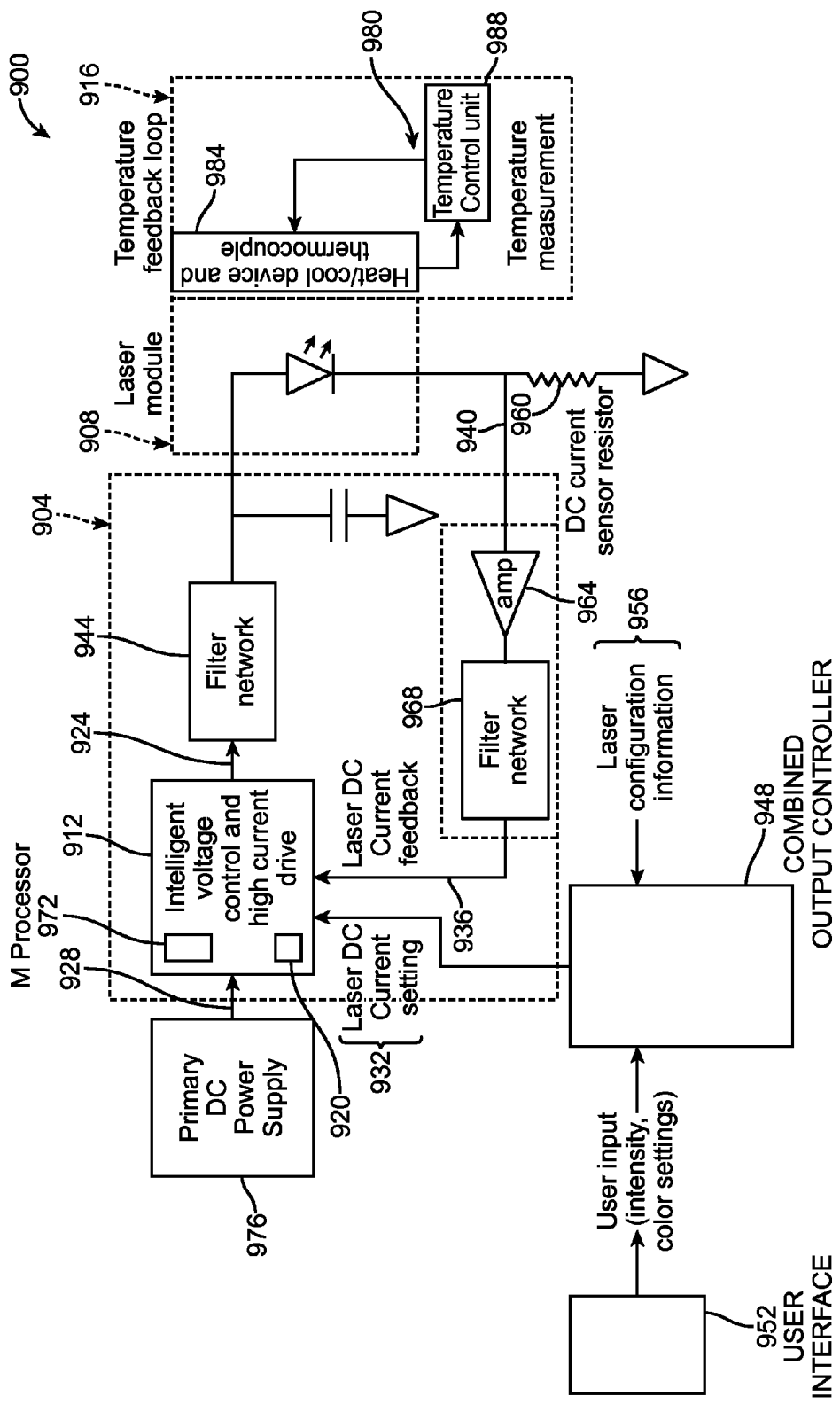
FIG. 9 is a high-level schematic diagram of an EMR-output control system that can be used to regulate the output of, for example, any of the laser-based and light-emitting-diode-based light sources disclosed herein.

In an exemplary instantiation of an embodiment utilizing mixing of red, green, and blue beams to create white general-illumination light, such as, for example, in systems 200, 400, and 600, above, the output of red, green, and blue solid state lasers was combined into a single beam and delivered via a fiber optic bundle of 0.4 mm diameter. Each of the lasers was individually adjustable in its intensity allowing the white light created by their combination to be adjustable in its color and intensity such that a user could match any color rending desired. Each of the individual red, green, and blue laser sources consisted of twenty solid state lasers operating in parallel. As in the examples above, the light output from the 0.4 mm fiber bundle was especially suited for an endoscopic illumination system or as an illumination source for a microscope. FIG. 9 illustrates an exemplary EMR-output control system 900 that was used to control the outputs of the lasers to produce the desired effect in the combination of the individual colors.

Referring to FIG. 9, in the configuration shown EMR-output control system 900 includes module control circuitry 904 that is designed and configured to control a single laser module 908, which in the multi-laser laser source example in the immediately preceding paragraph can be any one of the laser sources containing the paralleled solid state lasers of a particular color. In that three-color example, those skilled in the art would readily appreciate that overall control system 900 would include three instantiations of module control circuitry 904, one for each of the colors. In each of these instantiations, the corresponding laser module 908 can include multiple emitting elements (e.g., multiple individual laser diodes). All three of the laser module control circuitries 904 can be identical to the one shown. While module 908 is denoted as a "laser module," those skilled in the art will recognize that the module can be of another type, such as an LED module or other EMR-emitting module.

Module control circuitry 904 includes power control circuitry 912 and temperature control circuitry 916. Turning first to power control circuitry 912, this circuitry is designed and configured to provide high-precision direct current (DC) power to laser module 908. Power control circuitry 912 includes an intelligent voltage controller and high current driver 920 that outputs power 924 as a function of input DC power 928, a set of current settings 932, and a current feedback signal 936 based on a sensed current 940 from laser module 908. A filter 944 is provided to smooth and filter power 924 delivered to laser module 908 to eliminate spikes in current and/or voltage that could cause the laser module to exceed its operating specifications. Those skilled in the art will be readily familiar with the types of filters suitable for filter 944 based on the specific laser module 908 used, as well as the quality of power 928 output by driver 920.

In this example, current settings 932 for each power control circuitry 912 (again, only one is shown for brevity) are provided by a combined output controller 948, which determines the proper settings based on user input for overall intensity and/or color of the combined output of laser module 908 and the two other laser modules not shown. As those skilled in the art will readily appreciate, a user can input such intensity and/or color selection using any suitable user interface 952, which can range from one or more physical selectors, such as knobs, buttons, switches, dials, sliders, etc., to soft controls, such as soft versions of physical selectors mentioned that are displayed on a display (e.g., touchscreen), or other soft selection feature(s), such as numerical input fields, hypertext-style selectors, etc.

Once a user has selected/set a desired output intensity and/or desired output color, combined output controller 948 uses such selection(s)/setting(s) to determine the appropriate values of current settings 932 to provide to each power control circuitry 912 such that each of the three laser modules 908 outputs an amount of its colored light such that the combination of the three colored outputs has the desired color and intensity as set by the user via user interface 952. As those skilled in the art will readily appreciate, combined output controller 948 can determine the proper values for each set of current settings 932 using stored parameters 956 that can be obtained from the manufacturer of the laser modules 908, such as maximum current, voltage, power, temperature coefficients of output intensity, and output efficiency of the laser module at various power settings. As those skilled in the art will understand, stored parameters can be input into combined output controller 948 and/or suitable memory device, using any suitable means, such as via a parameter-input interface, computer-readable media, or other digital data transfer means.

In this example, current feedback signal 936 is obtained from laser module 908 using a DC current sense resistor 960, an amplifier 964, and a filter 968, which filters noise from sensed current 940. Intelligent voltage controller/current driver 920 uses current setting 932 from combined output controller 948 and current feedback signal 936 to precisely calculate and generate the correct voltage to apply to laser module 908. In one embodiment, intelligent voltage controller/current driver 920 includes a microprocessor 972 for making the necessary calculations and for providing output power 924 based on input DC power 928. It is noted that input DC power 928 can be provided from any suitable power supply 976, which may be a power supply that provides DC power to only one laser module 908 or may be configured to provide power to all three laser modules, depending on the particular design. Intelligent voltage controller/current driver 920 protects the lasers (not shown) within laser module 908 by delivering very precise current and voltage to the laser module. The DC operation of laser module 908 reduces the potential for damaging tissue or other target exposed to the combined laser output.

Temperature control circuitry 916 includes a temperature control feedback loop 980 that includes a thermoelectric module 984 and a temperature control unit 988. Thermoelectric module 984 is in thermal communication with laser module 908, for example, via a suitable thermocouple (not shown), and is designed and configured to cool and/or heat the laser module as needed for the laser module to function properly. Temperature control unit 988 controls power provided to thermoelectric module 984 as a function of the temperature of laser module 908 as indicated to the temperature control unit 988 via a suitable temperature sensor. In the event that the temperature of laser module 908 exceeds operating specifications, temperature control unit 988 has the capability to cause intelligent voltage controller/current driver 920 to turn off power 924 to shut down the laser module. It is noted that those skilled in the art will readily understand that a system similar to EMR-output control system 900 of FIG. 9 can be implemented for controlling LED-based light sources.

It is well known that a single laser beam, due to its narrow wavelength source, can interfere with itself, creating bright and dark regions in an effect known as "speckle." Speckle can be reduced by introducing mechanical means as described in prior art. The use of multiple laser sources of each color, however, acts to prevent the formation of speckle, since the illumination source consists of not a single laser but of a number of lasers that can create a smoother average intensity. Additionally, the use of a single laser source, such as a krypton-ion laser, requires the use of a specially tuned mirror to generate a lasing effect of the correct color mix. In order to select another color mix, a new laser setup is required that is time consuming and expensive. The use of individual laser sources for each color allows for simple color selection by software and electronic control of each individual color. Furthermore, when individual laser sources are used, it is a simple matter to add or remove other wavelengths that may not be visible to the human eye to facilitate other types of analysis or work.

In another particular instantiation, the output of red, green, blue, and ultraviolet solid state lasers were combined into a single beam and delivered via a fiber optic bundle of 0.4 mm diameter. Additionally, using the same optical arrangement, an additional green and infrared laser was combined and delivered via an adjacent optical fiber, much like the example of system 800 of FIG. 8. Each of the lasers was individually adjustable, for example, using an EMR-output control system similar to EMR-output control system 900 of FIG. 9, in its intensity and allowed for the creation of visible white light, invisible ultraviolet radiation, visible green, and invisible infrared radiation. The visible white light was created by the combination of red, green, and blue lasers and adjustable in its color and intensity such that it was suitable for a human or color camera to visualize the object it illuminated. Invisible ultraviolet radiation was used as an excitation source for fluorescent examination of the object in combination with appropriate fluorescent stains, for example to detect certain indicators of cancer cells. A visible green laser was then used as a pointing source for the infrared laser that could be used as a means to heat detected cancer cells in order to cause their death. The red, green, blue and ultraviolet laser sources used for general illumination of the area of interest were delivered through an optical fiber or fiber bundle with selected lenses and numerical apertures to spread the light out upon its exit from the fiber to create a uniform illumination of the object. The visible green pointing laser and the invisible infrared radiation were delivered through a separate optical fiber or fiber bundle and a lens system that maintains the optical pinpoint beam of the lasers so that they could be focused on the area(s) of interest without spreading.

In yet another specific instantiation, the laser illumination source described previously as coupled to a microscope, was implemented using red, green, and blue lasers and a deuterium ultraviolet source, whereby the red, green and blue lasers were used to generate a white illumination source used for viewing a fluorescent stained sample placed in the microscope field of view. After positioning the sample (target), the white illumination source could be turned off and the ultraviolet spectra of the deuterium source may be turned on to excite the fluorescent dye whose image is then captured by an imaging system.

Figure 10:
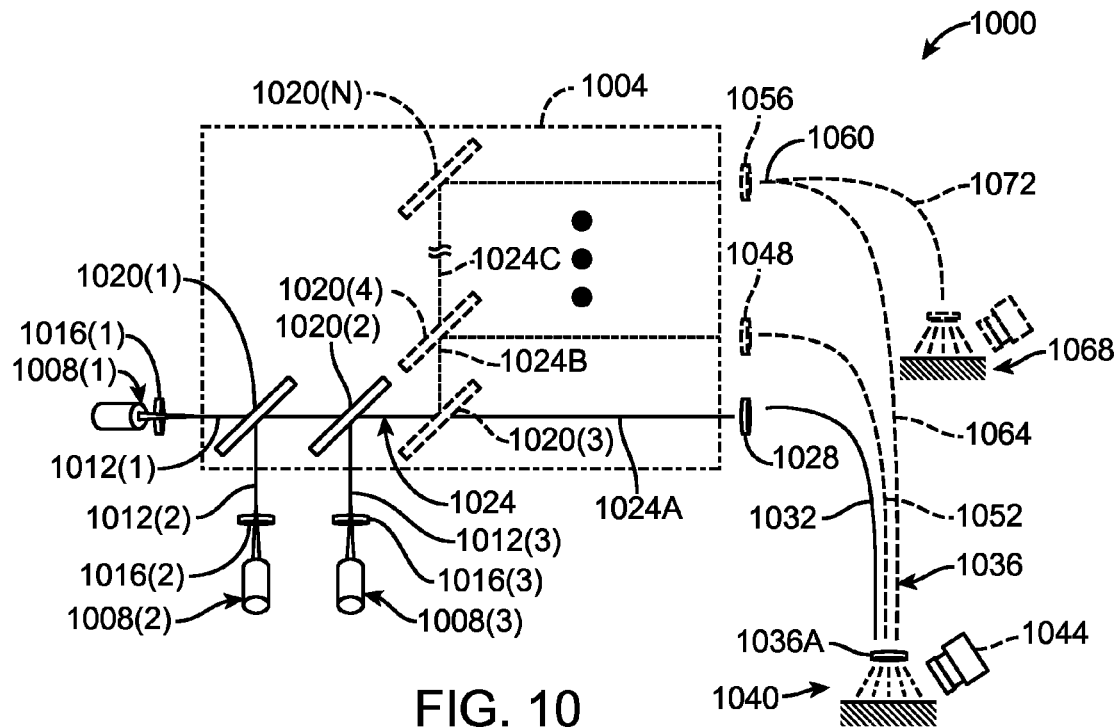
FIG. 10 is a diagram of an eighth exemplary system based on the system of FIG. 1 that includes red, green, and blue light sources and that illustrates several multichannel features.

FIG. 10 illustrates a system 1000 that includes an EMR-combiner 1004 and three light sources 1008, particularly in this embodiment a red light source 1008(1), a green light source 1008(2), and a blue light source 1008(3) that emit, respectively, a red light beam 1012(1), a green light beam 1012(2), and a blue light beam 1012(3). In accordance with the foregoing, each light source 1008 typically includes one or more individual light emitting elements (not shown), such as one or more LEDs or one or more laser diodes, for example, and a corresponding control circuitry, such as module control circuitry 904 of FIG. 9. Each light source 1008 may also include a corresponding focusing optic 1016, here focusing optics 1016(1), 1016(2), and 1016(3). In alternative embodiments, focusing optics 1016 may be provided as elements separate from light sources 1008.

In one example, EMR combiner 1004 includes a pair of mirrors 1020(1) and 1020(2) each designed and configured to pass at least a portion of red light beam 1012(1). Mirror 1020(1) is also designed and configured to reflect at least a portion of green light beam 1012(2), and mirror 1020(2) is also designed and configured to pass at least a portion of the green light beam 1012(2) as well as reflect at least a portion of blue light beam 1012(3), so as to create a combined beam 1024 that is a mixture of red, green, and blue light. Mirrors 1020(1) and 1020(2) can be selected or tuned in conjunction with the tuning of the intensity of individual light sources 1008, for example, via the corresponding module control circuitry (not shown, but see, e.g., system 900 of FIG. 9), to tune the color and/or other character of combined beam 1024 to suit the particular application at hand.

In one embodiment illustrated in FIG. 10, as in other embodiments disclosed herein, combined beam 1024 can be directed, for example, via a suitable output optic 1028, into an optical conduit 1032, such as an optical fiber or plurality of fibers. Such conduit 1032 can be part of a tool, such as an endoscope 1036, as is the case here, that includes an optic 1036A for spreading light to illuminate a target region 1040. Also as with other embodiments, overall system 1000 may include any suitable imaging device 1044.

As also illustrated in FIG. 10, the basic three-source system 1000 just described can be modified in a number of ways. For example, by adding a third beam-splitting mirror 1020(3) in the path of combined beam 1024, the combined beam can be split into a first portion 1024A and a second portion 1024B, each containing light that is a function of the light in the combined beam and the absorbing/transmitting and reflecting properties of third mirror 1020(3). As illustrated in FIG. 10, first portion 1024A of combined beam 1024 can be directed to output optic 1028 as describe above. Second portion 1024B of combined beam 1024 can be directed, for example, to a fourth mirror 1020(4), which can be either totally reflective or partially reflective. If fourth mirror 1020(4) is totally reflective, second portion 1024B of combined beam 1024 can be used, for example, as a redundant beam to first portion 1024A of the combined beam. In such case, second portion 1024B of combined beam 1024 can be directed to endoscope 1036 via a suitable output optic 1048. In this case, endoscope 1036 could include a separate optical conduit 1052 (e.g., optical fiber or fiber bundle) that directs the second portion of the combined beam to optic 1036. This can be useful, for example, for critical procedures, such as certain types of surgery, where interruptions due to malfunctioning equipment need to be minimized. With redundancy of optical paths through optical conduits 1032 and 1052, one can malfunction (e.g., break) and the other can provide a backup so that the procedure can continue.

As further illustrated in FIG. 10, system 1000 can be further augmented with any suitable number of additional mirrors/beamsplitters up to and including mirror 1020(N), with zero to N-5 mirrors/beamsplitters being located between mirror 1020(N) and mirror/beamsplitter 1020(4). In the example shown, mirror 1020(4) is a beamsplitting mirror that passes a third portion 1024C of combined beam 1024 to mirror 1020(N), which then directs the third portion to an output optic 1056. The output light 1060 of output optic 1056 can be used for a variety of purposes, such as to provide further redundancy to endoscope 1036 via another optical conduit 1064 or to provide illumination at another region 1068, for example, via another optical conduit 1072, or both.

Figure 11:
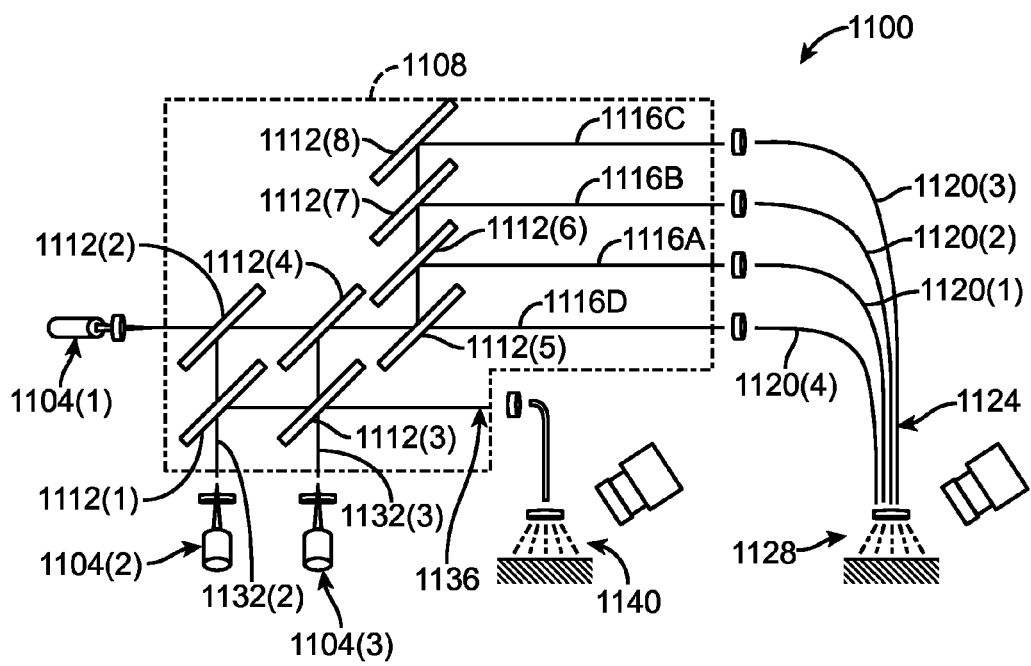
FIG. 11 is a diagram of a ninth exemplary system based on the system of FIG. 1 that includes three EMR sources and multiple EMR-combiner outputs.

FIG. 11 illustrates another exemplary system 1100 that contains three EMR source 1104(1) to 1104(3). For the sake of illustration, light sources 1104(1) to 1104(3) are red, green, and blue light sources, respectively, and can be the same as corresponding respective light sources 1008(1) to 1008(3) of system 1000 of FIG. 10. System 1100 of FIG. 11 includes an EMR (light) combiner 1108 that contains eight mirrors/beamsplitters 1112(1) to 1112(8) arranged as shown. In this example, mirrors/beamsplitters 1112(6) to 1112(8) direct corresponding respective portions 1116A to 1116C of a combined beam 1116 to optical conduits 1120(1) to 1120(3), and portion 1116D is directed to optical conduit 1120(4). Optical conduits 1120(1) to 1112(4), which, for example, may be composed of single optical fibers or fiber bundles, can be combined into a single tool, such as an endoscope 1124 used to illuminate a target region 1128, which may include one or more fluorophores or other absorptive/emissive materials. Mirrors/beamsplitters 1112(1) and 1112(3) in this example are used to combine the output beams 1132(2) and 1132(3) of only light sources 1104(2) and 1104(3) into a second combined beam 1136, which is directed to another target region 1140, which also may include one or more fluorophores or other absorptive/emissive materials. In this connection, those skilled in the art will readily appreciate that the character of portions 1116A to 1116D of combined beam 1116 can be tuned with the tuning of red, green, and blue light sources 1104(1) to 1104(3) and with the selection/tuning of the absorption/transmittance and reflectivities of mirrors/beamsplitters 1112(1) to 1112(8).

Indeed, using an EMR combiner, such as EMR combiner 1108, combined beam 1116 can be divided into any number of arbitrary beams, each of an arbitrary optical power. Such divided beams can be used to excite various fluorophores. When red, green, and blue light sources of certain wavelengths are used, such as in system 1100 of FIG. 11, these wavelengths are sufficient to excite about 75% of all commonly available fluorophores, making such a system a very cost effective source for fluorescence microscopy. In addition, the configuration of any EMR combiner made in accordance with the present disclosure can be tuned to the specific requirements of the output radiation, for example to maintain coherency or polarization on one output and purposely remove coherency or polarization on another.

In fluorescence imaging, usually the light sources are very weak so that the wavelength they emit is matched closely to the absorption fluorophores they need to excite. In another embodiment, a laser source that is very bright but not so well matched to absorption of the fluorophores is selected as one of the light sources. The extra power overcomes the poor absorption and delivers a strong emitted signal. In one example, the system is configured as follows. A blue laser source is matched to a blue fluorophore, a green laser source is matched to a green fluorophore, and a red laser source is split into two channels via a partially reflective mirror—a first red channel is matched to a red fluorophore, and a second red channel is not well matched to another red fluorophore, but the intensity of the laser still delivers a strong emission.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for applying focused electromagnetic radiation (EMR) to a target so as to perform work on the target, comprising:
    an illuminating-light source designed and configured to provide illuminating light;
    a work-EMR source designed and configured to provide a work-EMR beam;
    a pointing-light source designed and configured to provide a pointing-light beam;
    a tool that comprises:
        a first EMR input;
        a second EMR input;
        a work end that includes:
            a negative lens designed and configured for diverging the illuminating light so as to illuminate the target; and
            a positive lens designed and configured for focusing the work-EMR beam and the pointer-light beam so that the pointing-light beam indicates the location of the work-EMR beam;
        a first EMR conduit extending between said first EMR input and said negative lens; and
        a second EMR conduit extending between said second EMR input and said positive lens; and
    an EMR-guide designed and configured to:
        guide the illuminating light to the first EMR input; and
        combine the work-EMR beam and the pointing-light beam with one another and guide the work-EMR beam and the pointing-light beam to the second EMR input.

2. A system according to claim 1, wherein said illumination light source comprises a plurality of colored-light sources for providing differing-color-light beams that, when combined, form a white-light beam, and said EMF-guide is designed and configured to combine the differing-color-light beams into the white-light beam and provide the white-light beam to the first EMR input.

3. A system according to claim 2, wherein each of said plurality of colored-light sources comprises a laser.

4. A system according to claim 3, wherein each said laser comprises a solid-state laser.

5. A system according to claim 3, wherein said illuminating-light source further comprises an incoherent light source.

6. A system according to claim 1, wherein said work-EMR source comprises an infrared-light source.

7. A system according to claim 6, wherein said infrared-light source comprises a solid-state laser.

8. A system according to claim 6, wherein said pointing-light source comprises a laser.

9. A system according to claim 8, wherein said laser is a green laser.

10. A system according to claim 1, further comprising an imaging tool designed, configured, and located so as to provide an image of the illumination region.

11. A system according to claim 10, wherein said imaging tool comprises an image capturing tool.

12. A system according to claim 10, wherein said imaging tool is designed and configured to provide a live-view image.

13. A system according to claim 1, further comprising an analytical machine designed, configured, and located to as to capture analytical data from the illumination region.

* * * * *